(12) United States Patent
Padayachee et al.

(10) Patent No.: US 11,572,547 B2
(45) Date of Patent: Feb. 7, 2023

(54) FUSION PROTEINS FOR THE DETECTION OF APOPTOSIS

(71) Applicant: UNIVERSITY OF CAPE TOWN, Cape Town (ZA)

(72) Inventors: Eden Padayachee, Cape Town (ZA); Fleury Augustin Nsole Biteghe, Cape Town (ZA); Olusiji Alex Akinrinmade, Cape Town (ZA); Sandra Jordaan, Cape Town (ZA); Stefan Barth, Green Point (ZA)

(73) Assignee: UNIVERSITY OF CAPE TOWN, Cape Town (ZA)

( * ) Notice: Subject to any disclaimer, the term of this patent is extended or adjusted under 35 U.S.C. 154(b) by 423 days.

(21) Appl. No.: 16/770,551

(22) PCT Filed: Dec. 6, 2018

(86) PCT No.: PCT/IB2018/059704
§ 371 (c)(1),
(2) Date: Jun. 5, 2020

(87) PCT Pub. No.: WO2019/111194
PCT Pub. Date: Jun. 13, 2019

(65) Prior Publication Data
US 2021/0163899 A1 Jun. 3, 2021

(30) Foreign Application Priority Data

Dec. 6, 2017 (GB) .................................... 1720358

(51) Int. Cl.
| | | |
|---|---|---|
| C07K 14/47 | (2006.01) | |
| C12N 9/10 | (2006.01) | |
| C12N 15/62 | (2006.01) | |
| G01N 33/569 | (2006.01) | |
| G01N 33/573 | (2006.01) | |

(52) U.S. Cl.
CPC ............ *C12N 9/1007* (2013.01); *C07K 14/47* (2013.01); *C12N 15/62* (2013.01); *C12Y 201/01063* (2013.01); *G01N 33/56966* (2013.01); *G01N 33/573* (2013.01); *C07K 2319/21* (2013.01); *C07K 2319/50* (2013.01); *G01N 2333/91017* (2013.01); *G01N 2510/00* (2013.01)

(58) Field of Classification Search
CPC C07K 14/47; C07K 2319/02; C07K 2319/21; C07K 2319/50; C12N 15/62; C12Q 1/48
See application file for complete search history.

(56) References Cited

FOREIGN PATENT DOCUMENTS

| WO | WO 99/19470 A2 | 4/1999 |
| WO | WO 2009/013359 A2 | 1/2009 |
| WO | WO 2015/001078 A1 | 1/2015 |
| WO | WO 2017/118764 A1 | 7/2017 |

OTHER PUBLICATIONS

Pearson et al. 2005; Inhibition of O6-methylguantine DNA methyltransferase by an alkyltransferase-like protein from *Escherichia coli*. Nucleic acids Research. 33(12): 3837-3844.*
Juillerat et al. 2007; S-alkylation of O6-methylguantine DNA methyltransferase(MGMT) to sensitize cancer cells to anticancer therapy. Expert Ionin. Ther. Targets. 11(3): 349-361.*
Margison et al. Variability and regulation of O6-alkylguantine DNA alkyltransferase. Carcinogenesis. 24(4): 625-635.*
Combined Search and Examination Report Under Section 17 and 18(3) dated Dec. 21, 2017 in GB Application No. GB1720358.9.
International Preliminary Report on Patentability, dated Jan. 27, 2020, in International Application No. PCT/IB2018/059704.
International Search Report and Written Opinion, dated Mar. 19, 2019, in International Application No. PCT/IB2018/059704.
Kampmeier et al., Site-Specific, Covalent Labeling of Recombinant Antibody Fragment via Fusison to an engineered Version of 6-O Alkylguanine DNA Alkyltransferase, Bioconjugate Chemical, vol. 20, pp. 1010-1015, 2009.
New England Biolabs Inc., 2008, "SNAP-tag technologies: Novel tools to study protein function", Available from: https://www.neb.com/toolsand-resources/feature-articles/snap-tag-technologies-novel-tools-tostudy-protein-function.
Sateriale et al., SNAP-Tag Technology Optimized for Use in Entamoeba histolytica, PLOS One, vol. 8, No. 12, 2013.
Sun et al., Development of SNAP-Tag Fluorogenic Probes for Wash-Free Fluorescence Imaging Chembiochem, vol. 12, No. 14, pp. 2217-2226, 2011.
Tirat et al., Evaluation Of Two Novel Tag-Based Labelling Technologies For Site-Specific Modification Of Proteins International Journal Of Biological Mac Romo Lecu Les, vol. 39, No. 1-3, 2006.

(Continued)

Primary Examiner — Karen Cochrane Carlson
(74) Attorney, Agent, or Firm — Knobbe, Martens, Olson & Bear LLP

(57) ABSTRACT

The present invention relates to fusion proteins which are capable of binding to phosphatidylserine comprising a phosphatidylserene binding ligand and a modified O6-alkylguanine-DNA alkyltransferase which is capable of autoconjugation to an O6-benzylguanine-modified label, the fusion proteins being capable of binding to phosphatidylserine on the surface of a cell undergoing apoptosis. The invention also relates to recombinant polypeptide precursors of the fusion proteins which comprise a secretion leader sequence, purification tag, protease cleavage site and the fusion protein. Also included in the scope of the invention are nucleic acids encoding the recombinant polypeptide precursor, vectors comprising the nucleic acids, host cells comprising the vectors, methods of production of the fusion proteins, kits and assays for detecting apoptosis.

22 Claims, 6 Drawing Sheets
Specification includes a Sequence Listing.

(56) References Cited

OTHER PUBLICATIONS

Vermes et al., A Novel Assay For Apoptosis Flow Cytometric Detection Of Phosphatidylserine Expression On Early Apoptotic Cells Using Fluorescein Labelled Annexin V, Journal Of Immunological Methods, Elsevier Science Publishers B.V., Amsterdam, Nl, vol. 184, No. 1, pp. 39-51, 1995.

* cited by examiner

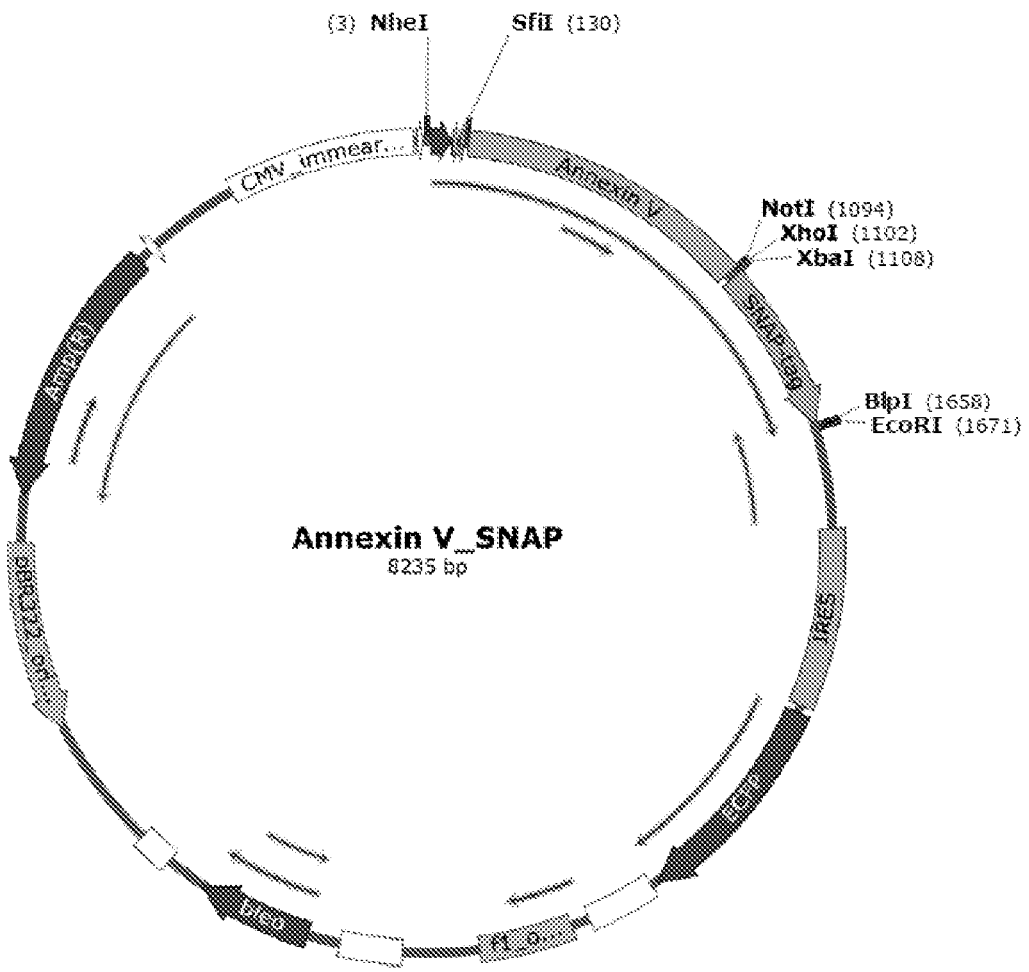

Figure 1

METDTLLLWVLLLWVPGSTGDAAHHHHHHAADDDDKAAQPAAQVLRGTVTDFPGFDERADAETLRKAMK
GLGTDEESILTLLTSRSNAQRQEISAAFKTLFGRDLLDDLKSELTGKFEKLIVALMKPSRLYDAYELKH
ALKGAGTNEKVLTEIIASRTPEELRAIKQVYEEEYGSSLEDDVVGDTSGYYQRMLVVLLQANRDPDAGI
DEAQVEQDAQALFQAGELKWGTDEEKFITIFGTRSVSHLRKVFDKYMTISGFQIEETIDRETSGNLEQL
LLAVVKSIRSIPAYLAETLYYAMKGAGTDDHTLIRVMVSRSEIDLFNIRKEFRKNFATSLYSMIKGDTS
GDYKKALLLLCGEDDAAASRMDKDCEMKRTTLDSPLGKLELSGCEQGLHEIKLLGKGTSAADAVEVPAP
AAVLGGPEPLMQATAWLNAYFHQPEAIEEFPVPALHHPVFQQESFTRQVLWKLLKVVKFGEVISYQQLA
ALAGNPAATAAVKTALSGNPVPILIPCHRVVSSSGAVGGYEGGLAVKEWLLAHEGHRLGKPGLAEH*

Figure 2

ATGGAGACAGACACACTCCTGCTATGGGTACTGCTGCTCTGGGTTCCAGGTTCCACTGGTGACGCCGCC
CATCATCATCATCATCATGCCGCCGACGACGACGACAAGGCGGCCCAGCCGGCCGCACAGGTTCTCAGA
GGCACTGTGACTGACTTCCCTGGATTTGATGAGCGGGCTGATGCAGAAACTCTTCGGAAGGCTATGAAA
GGCTTGGGCACAGATGAGGAGAGCATCCTGACTCTGTTGACATCCCGAAGTAATGCCCAGCGCCAGGAA
ATCTCTGCAGCTTTTAAGACTCTGTTTGGCAGGGATCTTCTGGATGACCTGAAATCAGAACTAACTGGA
AAATTTGAAAAATTAATTGTGGCTCTGATGAAACCCTCTCGGCTTTATGATGCTTATGAACTGAAACAT
GCCTTGAAGGGAGCTGGAACAAATGAAAAGTACTGACAGAAATTATTGCTTCAAGGACACCTGAAGAA
CTGAGAGCCATCAAACAAGTTTATGAAGAAGAATATGGCTCAAGCCTGGAAGATGACGTGGTGGGGGAC
ACTTCAGGGTACTACCAGCGGATGTTGGTGGTTCTCCTTCAGGCTAACAGAGACCCTGATGCTGGAATT
GATGAAGCTCAAGTTGAACAAGATGCTCAGGCTTTATTTCAGGCTGGAGAACTTAAATGGGGACAGAT
GAAGAAAAGTTTATCACCATCTTTGGAACACGAAGTGTGTCTCATTTGAGAAAGGTGTTTGACAAGTAC
ATGACTATATCAGGATTTCAAATTGAGGAAACCATTGACCGCGAGACTTCTGGCAATTTAGAGCAACTA
CTCCTTGCTGTTGTGAAATCTATTCGAAGTATACCTGCCTACCTTGCAGAGACCCTCTATTATGCTATG
AAGGGAGCTGGGACAGATGATCATACCCTCATCAGAGTCATGGTTTCCAGGAGTGAGATTGATCTGTTT
AACATCAGGAAGGAGTTTAGGAAGAATTTTGCCACCTCTCTTTATTCCATGATTAAGGGAGATACATCT
GGGGACTATAAGAAAGCTCTTCTGCTGCTCTGTGGAGAAGATGACGCGGCCGCTTCTAGAATGGACAAA
GACTGCGAAATGAAGCGCACCACCCTGGATAGCCCTCTGGGCAAGCTGGAACTGTCTGGGTGCGAACAG
GGCCTGCACGAGATCAAGCTGCTGGGCAAAGGAACATCTGCCGCCGACGCCGTGGAAGTGCCTGCCCCA
GCCGCCGTGCTGGGCGGACCAGAGCCACTGATGCAGGCCACCGCCTGGCTCAACGCCTACTTTCACCAG
CCTGAGGCCATCGAGGAGTTCCCTGTGCCAGCCCTGCACCACCCAGTGTTCCAGCAGGAGAGCTTTACC
CGCCAGGTGCTGTGGAAACTGCTGAAAGTGGTGAAGTTCGGAGAGGTCATCAGCTACCAGCAGCTGGCG
GCCCTGGCGGGCAATCCCGCCGCCACCGCCGCCGTGAAAACCGCCCTGAGCGGAAATCCCGTGCCCATT
CTGATCCCCTGCCACCGGGTGGTGTCTAGCTCTGGCGCCGTGGGGGGCTACGAGGGCGGGCTCGCCGTG
AAAGAGTGGCTGCTGGCCCACGAGGGCCACAGACTGGGCAAGCCTGGGCTGGCTGAGCACTGA

Figure 4

AAQPAAQVLRGTVTDFPGFDERADAETLRKAMKGLGTDEESILTLLTSRSNAQRQEISAAFKTLFGRDL
LDDLKSELTGKFEKLIVALMKPSRLYDAYELKHALKGAGTNEKVLTEIIASRTPEELRAIKQVYEEEYG
SSLEDDVVGDTSGYYQRMLVVLLQANRDPDAGIDEAQVEQDAQALFQAGELKWGTDEEKFITIFGTRSV
SHLRKVFDKYMTISGFQIEETIDRETSGNLEQLLLAVVKSIRSIPAYLAETLYYAMKGAGTDDHTLIRV
MVSRSEIDLFNIRKEFRKNFATSLYSMIKGDTSGDYKKALLLLCGEDDAAASRMDKDCEMKRTTLDSPL
GKLELSGCEQGLHEIKLLGKGTSAADAVEVPAPAAVLGGPEPLMQATAWLNAYFHQPEAIEEFPVPALH
HPVFQQESFTRQVLWKLLKVVKFGEVISYQQLAALAGNPAATAAVKTALSGNPVPILIPCHRVVSSSGA
VGGYEGGLAVKEWLLAHEGHRLGKPGLAEH

Figure 5

```
GGCCCAGCCGGCCGCACAGGTTCTCAGAGGCACTGTGACTGACTTCCCTGGATTTGATGAGCGGGCTGA
TGCAGAAACTCTTCGGAAGGCTATGAAAGGCTTGGGCACAGATGAGGAGAGCATCCTGACTCTGTTGAC
ATCCCGAAGTAATGCCCAGCGCCAGGAAATCTCTGCAGCTTTTAAGACTCTGTTTGGCAGGGATCTTCT
GGATGACCTGAAATCAGAACTAACTGGAAAATTTGAAAAATTAATTGTGGCTCTGATGAAACCCTCTCG
GCTTTATGATGCTTATGAACTGAAACATGCCTTGAAGGGAGCTGGAACAAATGAAAAGTACTGACAGA
ATTATTGCTTCAAGGACACCTGAAGAACTGAGAGCCATCAAACAAGTTTATGAAGAAGAATATGGCTC
AAGCCTGGAAGATGACGTGGTGGGGGACACTTCAGGGTACTACCAGCGGATGTTGGTGGTTCTCCTTCA
GGCTAACAGAGACCCTGATGCTGGAATTGATGAAGCTCAAGTTGAACAAGATGCTCAGGCTTTATTTCA
GGCTGGAGAACTTAAATGGGGACAGATGAAGAAAGTTTATCACCATCTTTGGAACACGAAGTGTGTC
TCATTTGAGAAAGGTGTTTGACAAGTACATGACTATATCAGGATTTCAAATTGAGGAAACCATTGACCG
CGAGACTTCTGGCAATTTAGAGCAACTACTCCTTGCTGTTGTGAAATCTATTCGAAGTATACCTGCCTA
CCTTGCAGAGACCCTCTATTATGCTATGAAGGGAGCTGGGACAGATGATCATACCCTCATCAGAGTCAT
GGTTTCCAGGAGTGAGATTGATCTGTTTAACATCAGGAAGGAGTTTAGGAAGAATTTTGCCACCTCTCT
TTATTCCATGATTAAGGGAGATACATCTGGGGACTATAAGAAAGCTCTTCTGCTGCTCTGTGGAGAAGA
TGACGCGGCCGC
```

Figure 6

```
AQVLRGTVTDFPGFDERADAETLRKAMKGLGTDEESILTLLTSRSNAQRQEISAAFKTLFGRDLLDDLK
SELTGKFEKLIVALMKPSRLYDAYELKHALKGAGTNEKVLTEIIASRTPEELRAIKQVYEEEYGSSLED
DVVGDTSGYYQRMLVVLLQANRDPDAGIDEAQVEQDAQALFQAGELKWGTDEEKFITIFGTRSVSHLRK
VFDKYMTISGFQIEETIDRETSGNLEQLLLAVVKSIRSIPAYLAETLYYAMKGAGTDDHTLIRVMVSRS
EIDLFNIRKEFRKNFATSLYSMIKGDTSGDYKKALLLLCGEDD
```

Figure 7

```
ATGGACAAAGACTGCGAAATGAAGCGCACCACCCTGGATAGCCCTCTGGGCAAGCTGGAACTGTCTGGG
TGCGAACAGGGCCTGCACGAGATCAAGCTGCTGGGCAAAGGAACATCTGCCGCCGACGCCGTGGAAGTG
CCTGCCCCAGCCGCCGTGCTGGGCGGACCAGAGCCACTGATGCAGGCCACCGCCTGGCTCAACGCCTAC
TTTCACCAGCCTGAGGCCATCGAGGAGTTCCCTGTGCCAGCCCTGCACCACCCAGTGTTCCAGCAGGAG
AGCTTTACCCGCCAGGTGCTGTGGAAACTGCTGAAAGTGGTGAAGTTCGGAGAGGTCATCAGCTACCAG
CAGCTGGCGGCCCTGGCGGGCAATCCCGCCGCCACCGCCGCCGTGAAAACCGCCCTGAGCGGAAATCCC
GTGCCCATTCTGATCCCCTGCCACCGGGTGGTGTCTAGCTCTGGCGCCGTGGGGGCTACGAGGGCGGG
CTCGCCGTGAAAGAGTGGCTGCTGGCCCACGAGGGCCACAGACTGGGCAAGCCTGGGCTG
```

Figure 8

MDKDCEMKRTTLDSPLGKLELSGCEQGLHEIKLLGKGTSAADAVEVPAPAAVLGGPEPLMQATAWLNAY
FHQPEAIEEFPVPALHHPVFQQESFTRQVLWKLLKVVKFGEVISYQQLAALAGNPAATAAVKTALSGNP
VPILIPCHRVVSSSGAVGGYEGGLAVKEWLLAHEGHRLGKPGL

Figure 9

METDTLLLWVLLLWVPGSTGDAAHHHHHHAADDDDKAAQPAAQVLRGTVTDFPGFDERADAETLRKAMK
GLGTDEESILTLLTSRSNAQRQEISAAFKTLFGRDLLDDLKSELTGKFEKLIVALMKPSRLYDAYELKH
ALKGAGTNEKVLTEIIASRTPEELRAIKQVYEEEYGSSLEDDVVGDTSGYYQRMLVVLLQANRDPDAGI
DEAQVEQDAQALFQAGELKWGTDEEKFITIFGTRSVSHLRKVFDKYMTISGFQIEETIDRETSGNLEQL
LLAVVKSIRSIPAYLAETLYYAMKGAGTDDHTLIRVMVSRSEIDLFNIRKEFRKNFATSLYSMIKGDTS
GDYKKALLLLCGEDDAAALESRMDKDCEMKRTTLDSPLGKLELSGCEQGLHEIKLLGKGTSAADAVEVP
APAAVLGGPEPLMQATAWLNAYFHQPEAIEEFPVPALHHPVFQQESFTRQVLWKLLKVVKFGEVISYQQ
LAALAGNPAATAAVKTALSGNPVPILIPCHRVVSSSGAVGGYEGGLAVKEWLLAHEGHRLGKPGLAEH

Figure 10

```
ATGGAGACAGACACACTCCTGCTATGGGTACTGCTGCTCTGGGTTCCAGGTTCCACTGGTGACGCCGCC
CATCATCATCATCATCATGCCGCCGACGACGACGACAAGGCGGCCCAGCCGGCCGCACAGGTTCTCAGA
GGCACTGTGACTGACTTCCCTGGATTTGATGAGCGGGCTGATGCAGAAACTCTTCGGAAGGCTATGAAA
GGCTTGGGCACAGATGAGGAGAGCATCCTGACTCTGTTGACATCCCGAAGTAATGCCCAGCGCCAGGAA
ATCTCTGCAGCTTTTAAGACTCTGTTTGGCAGGGATCTTCTGGATGACCTGAAATCAGAACTAACTGGA
AAATTTGAAAAATTAATTGTGGCTCTGATGAAACCCTCTCGGCTTTATGATGCTTATGAACTGAAACAT
GCCTTGAAGGGAGCTGGAACAAATGAAAAGTACTGACAGAAATTATTGCTTCAAGGACACCTGAAGAA
CTGAGAGCCATCAAACAAGTTTATGAAGAAGAATATGGCTCAAGCCTGGAAGATGACGTGGTGGGGGAC
ACTTCAGGGTACTACCAGCGGATGTTGGTGGTTCTCCTTCAGGCTAACAGAGACCCTGATGCTGGAATT
GATGAAGCTCAAGTTGAACAAGATGCTCAGGCTTTATTTCAGGCTGGAGAACTTAAATGGGGACAGAT
GAAGAAAAGTTTATCACCATCTTTGGAACACGAAGTGTGTCTCATTTGAGAAAGGTGTTTGACAAGTAC
ATGACTATATCAGGATTTCAAATTGAGGAAACCATTGACCGCGAGACTTCTGGCAATTTAGAGCAACTA
CTCCTTGCTGTTGTGAAATCTATTCGAAGTATACCTGCCTACCTTGCAGAGACCCTCTATTATGCTATG
AAGGGAGCTGGGACAGATGATCATACCCTCATCAGAGTCATGGTTTCCAGGAGTGAGATTGATCTGTTT
AACATCAGGAAGGAGTTTAGGAAGAATTTTGCCACCTCTCTTTATTCCATGATTAAGGGAGATACATCT
GGGGACTATAAGAAAGCTCTTCTGCTGCTCTGTGGAGAAGATGACGCGGCCGCACTCGAGTCTAGAATG
GACAAAGACTGCGAAATGAAGCGCACCACCCTGGATAGCCCTCTGGGCAAGCTGGAACTGTCTGGGTGC
GAACAGGGCCTGCACGAGATCAAGCTGCTGGGCAAAGGAACATCTGCCGCCGACGCCGTGGAAGTGCCT
GCCCCAGCCGCCGTGCTGGGCGGACCAGAGCCACTGATGCAGGCCACCGCCTGGCTCAACGCCTACTTT
CACCAGCCTGAGGCCATCGAGGAGTTCCCTGTGCCAGCCCTGCACCACCCAGTGTTCCAGCAGGAGAGC
TTTACCCGCCAGGTGCTGTGGAAACTGCTGAAAGTGGTGAAGTTCGGAGAGGTCATCAGCTACCAGCAG
CTGGCGGCCCTGGCGGGCAATCCCGCCGCCACCGCCGCCGTGAAAACCGCCCTGAGCGGAAATCCCGTG
CCCATTCTGATCCCCTGCCACCGGGTGGTGTCTAGCTCTGGCGCCGTGGGGGGCTACGAGGGCGGGCTC
GCCGTGAAAGAGTGGCTGCTGGCCCACGAGGGCCACAGACTGGGCAAGCCTGGGCTGGCTGAGCACTGA
```

Figure 11

SEQUENCE LISTING

```
<160> NUMBER OF SEQ ID NOS: 16

<210> SEQ ID NO 1
<211> LENGTH: 549
<212> TYPE: PRT
<213> ORGANISM: Artificial sequence
<220> FEATURE:
<223> OTHER INFORMATION: First Generation Annexin A5 SNAP polypeptide
      precursor amino acid sequence

<400> SEQUENCE: 1

Met Glu Thr Asp Thr Leu Leu Leu Trp Val Leu Leu Leu Trp Val Pro
1               5                   10                  15

Gly Ser Thr Gly Asp Ala Ala His His His His His His Ala Ala Asp
            20                  25                  30

Asp Asp Asp Lys Ala Ala Gln Pro Ala Ala Gln Val Leu Arg Gly Thr
        35                  40                  45

Val Thr Asp Phe Pro Gly Phe Asp Glu Arg Ala Asp Ala Glu Thr Leu
    50                  55                  60

Arg Lys Ala Met Lys Gly Leu Gly Thr Asp Glu Glu Ser Ile Leu Thr
65                  70                  75                  80

Leu Leu Thr Ser Arg Ser Asn Ala Gln Arg Gln Glu Ile Ser Ala Ala
                85                  90                  95

Phe Lys Thr Leu Phe Gly Arg Asp Leu Leu Asp Asp Leu Lys Ser Glu
            100                 105                 110

Leu Thr Gly Lys Phe Glu Lys Leu Ile Val Ala Leu Met Lys Pro Ser
        115                 120                 125

Arg Leu Tyr Asp Ala Tyr Glu Leu Lys His Ala Leu Lys Gly Ala Gly
    130                 135                 140

Thr Asn Glu Lys Val Leu Thr Glu Ile Ile Ala Ser Arg Thr Pro Glu
145                 150                 155                 160

Glu Leu Arg Ala Ile Lys Gln Val Tyr Glu Glu Glu Tyr Gly Ser Ser
                165                 170                 175

Leu Glu Asp Asp Val Val Gly Asp Thr Ser Gly Tyr Tyr Gln Arg Met
            180                 185                 190

Leu Val Val Leu Leu Gln Ala Asn Arg Asp Pro Asp Ala Gly Ile Asp
        195                 200                 205

Glu Ala Gln Val Glu Gln Asp Ala Gln Ala Leu Phe Gln Ala Gly Glu
    210                 215                 220

Leu Lys Trp Gly Thr Asp Glu Glu Lys Phe Ile Thr Ile Phe Gly Thr
225                 230                 235                 240

Arg Ser Val Ser His Leu Arg Lys Val Phe Asp Lys Tyr Met Thr Ile
```

```
            245                 250                 255
Ser Gly Phe Gln Ile Glu Glu Thr Ile Asp Arg Glu Thr Ser Gly Asn
            260                 265                 270

Leu Glu Gln Leu Leu Leu Ala Val Val Lys Ser Ile Arg Ser Ile Pro
            275                 280                 285

Ala Tyr Leu Ala Glu Thr Leu Tyr Tyr Ala Met Lys Gly Ala Gly Thr
            290                 295                 300

Asp Asp His Thr Leu Ile Arg Val Met Val Ser Arg Ser Glu Ile Asp
305                 310                 315                 320

Leu Phe Asn Ile Arg Lys Glu Phe Arg Lys Asn Phe Ala Thr Ser Leu
            325                 330                 335

Tyr Ser Met Ile Lys Gly Asp Thr Ser Gly Asp Tyr Lys Lys Ala Leu
            340                 345                 350

Leu Leu Leu Cys Gly Glu Asp Asp Ala Ala Ser Arg Met Asp Lys
            355                 360                 365

Asp Cys Glu Met Lys Arg Thr Thr Leu Asp Ser Pro Leu Gly Lys Leu
370                 375                 380

Glu Leu Ser Gly Cys Glu Gln Gly Leu His Glu Ile Lys Leu Leu Gly
385                 390                 395                 400

Lys Gly Thr Ser Ala Ala Asp Ala Val Glu Val Pro Ala Pro Ala Ala
                    405                 410                 415

Val Leu Gly Gly Pro Glu Pro Leu Met Gln Ala Thr Ala Trp Leu Asn
                    420                 425                 430

Ala Tyr Phe His Gln Pro Glu Ala Ile Glu Glu Phe Pro Val Pro Ala
                    435                 440                 445

Leu His His Pro Val Phe Gln Gln Glu Ser Phe Thr Arg Gln Val Leu
        450                 455                 460

Trp Lys Leu Leu Lys Val Val Lys Phe Gly Glu Val Ile Ser Tyr Gln
465                 470                 475                 480

Gln Leu Ala Ala Leu Ala Gly Asn Pro Ala Ala Thr Ala Ala Val Lys
                    485                 490                 495

Thr Ala Leu Ser Gly Asn Pro Val Pro Ile Leu Ile Pro Cys His Arg
                    500                 505                 510

Val Val Ser Ser Ser Gly Ala Val Gly Gly Tyr Glu Gly Gly Leu Ala
            515                 520                 525

Val Lys Glu Trp Leu Leu Ala His Glu Gly His Arg Leu Gly Lys Pro
            530                 535                 540

Gly Leu Ala Glu His
545

<210> SEQ ID NO 2
<211> LENGTH: 1650
<212> TYPE: DNA
<213> ORGANISM: Artificial sequence
<220> FEATURE:
<223> OTHER INFORMATION: First Generation Annexin A5 SNAP polypeptide
      precursor nucleotide sequence

<400> SEQUENCE: 2
atggagacag acacactcct gctatgggta ctgctgctct gggttccagg ttccactggt     60
gacgccgccc atcatcatca tcatcatgcc gccgacgacg acgacaaggc ggcccagccg    120
gccgcacagg ttctcagagg cactgtgact gacttccctg gatttgatga gcgggctgat    180
gcagaaactc ttcggaaggc tatgaaaggc ttgggcacag atgaggagag catcctgact    240
ctgttgacat cccgaagtaa tgcccagcgc caggaaatct ctgcagcttt taagactctg    300
```

```
tttggcaggg atcttctgga tgacctgaaa tcagaactaa ctggaaaatt tgaaaaatta      360
attgtggctc tgatgaaacc ctctcggctt tatgatgctt atgaactgaa acatgccttg      420
aagggagctg aacaaatga aaaagtactg acagaaatta ttgcttcaag gacacctgaa       480
gaactgagag ccatcaaaca agtttatgaa gaagaatatg gctcaagcct ggaagatgac      540
gtggtggggg acacttcagg gtactaccag cggatgttgg tggttctcct tcaggctaac      600
agagaccctg atgctggaat tgatgaagct caagttgaac aagatgctca ggctttattt      660
caggctggag aacttaaatg ggggacagat gaagaaaagt ttatcaccat ctttggaaca      720
cgaagtgtgt ctcatttgag aaaggtgttt gacaagtaca tgactatatc aggatttcaa      780
attgaggaaa ccattgaccg cgagacttct ggcaatttag agcaactact ccttgctgtt      840
gtgaaatcta ttcgaagtat acctgcctac cttgcagaga ccctctatta tgctatgaag      900
ggagctggga cagatgatca taccctcatc agagtcatgg tttccaggag tgagattgat      960
ctgtttaaca tcaggaagga gtttaggaag aattttgcca cctctcttta ttccatgatt     1020
aagggagata catctgggga ctataagaaa gctcttctgc tgctctgtgg agaagatgac     1080
gcggccgctt ctagaatgga caaagactgc gaaatgaagc gcaccaccct ggatagccct     1140
ctgggcaagc tggaactgtc tgggtgcgaa cagggcctgc acgagatcaa gctgctgggc     1200
aaaggaacat ctgccgccga cgccgtggaa gtgcctgccc cagccgccgt gctgggcgga     1260
ccagagccac tgatgcaggc caccgcctgg ctcaacgcct actttcacca gcctgaggcc     1320
atcgaggagt ccctgtgtgcc agccctgcac acccagtgt tccagcagga gctttacc     1380 cgccaggtgc tgtggaaact gctgaaagtg gtgaagttcg gagaggtcat cagctaccag     1440
cagctggcgg ccctggcggg caatcccgcc gccaccgccg ccgtgaaaac cgccctgagc     1500
ggaaatcccg tgcccattct gatcccctgc accgggtgg tgtctagctc tggcgccgtg      1560
gggggctacg agggcgggct cgccgtgaaa gagtggctgc tggcccacga gggccacaga     1620
ctgggcaagc tgggctggc tgagcactga                                        1650
```

<210> SEQ ID NO 3
<211> LENGTH: 513
<212> TYPE: PRT
<213> ORGANISM: Artificial sequence
<220> FEATURE:
<223> OTHER INFORMATION: First Generation Annexin A5 SNAP mature
      polypeptide amino acid sequence

<400> SEQUENCE: 3

```
Ala Ala Gln Pro Ala Ala Gln Val Leu Arg Gly Thr Val Thr Asp Phe
1               5                   10                  15

Pro Gly Phe Asp Glu Arg Ala Asp Ala Glu Thr Leu Arg Lys Ala Met
                20                  25                  30

Lys Gly Leu Gly Thr Asp Glu Glu Ser Ile Leu Thr Leu Leu Thr Ser
            35                  40                  45

Arg Ser Asn Ala Gln Arg Gln Glu Ile Ser Ala Ala Phe Lys Thr Leu
        50                  55                  60

Phe Gly Arg Asp Leu Leu Asp Asp Leu Lys Ser Glu Leu Thr Gly Lys
65                  70                  75                  80

Phe Glu Lys Leu Ile Val Ala Leu Met Lys Pro Ser Arg Leu Tyr Asp
                85                  90                  95

Ala Tyr Glu Leu Lys His Ala Leu Lys Gly Ala Gly Thr Asn Glu Lys
            100                 105                 110
```

```
Val Leu Thr Glu Ile Ile Ala Ser Arg Thr Pro Glu Leu Arg Ala
            115                 120                 125
Ile Lys Gln Val Tyr Glu Glu Tyr Gly Ser Ser Leu Glu Asp Asp
        130                 135                 140
Val Val Gly Asp Thr Ser Gly Tyr Tyr Gln Arg Met Leu Val Leu
145                 150                 155                 160
Leu Gln Ala Asn Arg Asp Pro Asp Ala Gly Ile Asp Glu Ala Gln Val
                165                 170                 175
Glu Gln Asp Ala Gln Ala Leu Phe Gln Ala Gly Glu Leu Lys Trp Gly
            180                 185                 190
Thr Asp Glu Glu Lys Phe Ile Thr Ile Phe Gly Thr Arg Ser Val Ser
            195                 200                 205
His Leu Arg Lys Val Phe Asp Lys Tyr Met Thr Ile Ser Gly Phe Gln
        210                 215                 220
Ile Glu Glu Thr Ile Asp Arg Glu Thr Ser Gly Asn Leu Glu Gln Leu
225                 230                 235                 240
Leu Leu Ala Val Val Lys Ser Ile Arg Ser Ile Pro Ala Tyr Leu Ala
                245                 250                 255
Glu Thr Leu Tyr Tyr Ala Met Lys Gly Ala Gly Thr Asp Asp His Thr
            260                 265                 270
Leu Ile Arg Val Met Val Ser Arg Ser Glu Ile Asp Leu Phe Asn Ile
        275                 280                 285
Arg Lys Glu Phe Arg Lys Asn Phe Ala Thr Ser Leu Tyr Ser Met Ile
        290                 295                 300
Lys Gly Asp Thr Ser Gly Asp Tyr Lys Lys Ala Leu Leu Leu Leu Cys
305                 310                 315                 320
Gly Glu Asp Asp Ala Ala Ala Ser Arg Met Asp Lys Asp Cys Glu Met
                325                 330                 335
Lys Arg Thr Thr Leu Asp Ser Pro Leu Gly Lys Leu Glu Leu Ser Gly
            340                 345                 350
Cys Glu Gln Gly Leu His Glu Ile Lys Leu Leu Gly Lys Gly Thr Ser
        355                 360                 365
Ala Ala Asp Ala Val Glu Val Pro Ala Pro Ala Ala Val Leu Gly Gly
        370                 375                 380
Pro Glu Pro Leu Met Gln Ala Thr Ala Trp Leu Asn Ala Tyr Phe His
385                 390                 395                 400
Gln Pro Glu Ala Ile Glu Glu Phe Pro Val Pro Ala Leu His His Pro
                405                 410                 415
Val Phe Gln Gln Glu Ser Phe Thr Arg Gln Val Leu Trp Lys Leu Leu
            420                 425                 430
Lys Val Val Lys Phe Gly Glu Val Ile Ser Tyr Gln Gln Leu Ala Ala
        435                 440                 445
Leu Ala Gly Asn Pro Ala Ala Thr Ala Val Lys Thr Ala Leu Ser
        450                 455                 460
Gly Asn Pro Val Pro Ile Leu Ile Pro Cys His Arg Val Val Ser Ser
465                 470                 475                 480
Ser Gly Ala Val Gly Gly Tyr Glu Gly Gly Leu Ala Val Lys Glu Trp
                485                 490                 495
Leu Leu Ala His Glu Gly His Arg Leu Gly Lys Pro Gly Leu Ala Glu
            500                 505                 510
His

<210> SEQ ID NO 4
```

<211> LENGTH: 978
<212> TYPE: DNA
<213> ORGANISM: Artificial sequence
<220> FEATURE:
<223> OTHER INFORMATION: Modified Annexin A5 ORF nucleotide sequence with restriction sites

<400> SEQUENCE: 4

```
ggcccagccg gccgcacagg ttctcagagg cactgtgact gacttccctg gatttgatga    60
gcgggctgat gcagaaactc ttcggaaggc tatgaaaggc ttgggcacag atgaggagag   120
catcctgact ctgttgacat cccgaagtaa tgcccagcgc caggaaatct ctgcagcttt   180
taagactctg tttggcaggg atcttctgga tgacctgaaa tcagaactaa ctggaaaatt   240
tgaaaaatta attgtggctc tgatgaaacc ctctcggctt tatgatgctt atgaactgaa   300
acatgccttg aagggagctg gaacaaatga aaaagtactg acagaaatta ttgcttcaag   360
gacacctgaa gaactgagag ccatcaaaca gtttatgaa gaagaatatg gctcaagcct   420
ggaagatgac gtggtggggg cacttcagg gtactaccag cggatgttgg tggttctcct   480
tcaggctaac agagaccctg atgctggaat tgatgaagct caagttgaac aagatgctca   540
ggctttattt caggctggag aacttaaatg ggggacagat gaagaaaagt ttatcaccat   600
ctttggaaca cgaagtgtgt ctcatttgag aaaggtgttt gacaagtaca tgactatatc   660
aggatttcaa attgaggaaa ccattgaccg cgagacttct ggcaatttag agcaactact   720
ccttgctgtt gtgaaatcta ttcgaagtat acctgcctac cttgcagaga ccctctatta   780
tgctatgaag ggagctggga cagatgatca taccctcatc agagtcatgg tttccaggag   840
tgagattgat ctgtttaaca tcaggaagga gtttaggaag aattttgcca cctctcttta   900
ttccatgatt aagggagata catctgggga ctataagaaa gctcttctgc tgctctgtgg   960
agaagatgac gcggccgc                                                  978
```

<210> SEQ ID NO 5
<211> LENGTH: 319
<212> TYPE: PRT
<213> ORGANISM: Homo sapiens

<400> SEQUENCE: 5

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
```

```
                145                 150                 155                 160
Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
                180                 185                 190

Phe Ile Thr Ile Phe Gly Thr Arg Ser Val Ser His Leu Arg Lys Val
                195                 200                 205

Phe Asp Lys Tyr Met Thr Ile Ser Gly Phe Gln Ile Glu Glu Thr Ile
                210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
                260                 265                 270

Val Ser Arg Ser Glu Ile Asp Leu Phe Asn Ile Arg Lys Glu Phe Arg
                275                 280                 285

Lys Asn Phe Ala Thr Ser Leu Tyr Ser Met Ile Lys Gly Asp Thr Ser
                290                 295                 300

Gly Asp Tyr Lys Lys Ala Leu Leu Leu Leu Cys Gly Glu Asp Asp
305                 310                 315

<210> SEQ ID NO 6
<211> LENGTH: 543
<212> TYPE: DNA
<213> ORGANISM: Artificial sequence
<220> FEATURE:
<223> OTHER INFORMATION: SNAP-tag nucleotide sequence

<400> SEQUENCE: 6
atggacaaag actgcgaaat gaagcgcacc accctggata gccctctggg caagctggaa      60
ctgtctgggt gcgaacaggg cctgcacgag atcaagctgc tgggcaaagg aacatctgcc     120
gccgacgccg tggaagtgcc tgccccagcc gccgtgctgg gcggaccaga gccactgatg     180
caggccaccg cctggctcaa cgcctacttt caccagcctg aggccatcga ggagttccct     240
gtgccagccc tgcaccaccc agtgttccag caggagagct ttacccgcca ggtgctgtgg     300
aaactgctga aagtggtgaa gttcggagag gtcatcagct accagcagct ggcggccctg     360
gcgggcaatc ccgccgccac cgccgccgtg aaaaccgccc tgagcggaaa tcccgtgccc     420
attctgatcc cctgccaccg ggtggtgtct agctctggcg ccgtggggg ctacgagggc     480 gggctcgccg tgaaagagtg gctgctggcc cacgagggcc acagactggg caagcctggg     540
ctg                                                                    543

<210> SEQ ID NO 7
<211> LENGTH: 181
<212> TYPE: PRT
<213> ORGANISM: Artificial sequence
<220> FEATURE:
<223> OTHER INFORMATION: SNAP-tag amino acid sequence

<400> SEQUENCE: 7

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
                20                  25                  30

Leu Leu Gly Lys Gly Thr Ser Ala Ala Asp Ala Val Glu Val Pro Ala
```

```
            35                  40                  45
Pro Ala Val Leu Gly Gly Pro Glu Pro Leu Met Gln Ala Thr Ala
 50                  55                  60
Trp Leu Asn Ala Tyr Phe His Gln Pro Glu Ala Ile Glu Glu Phe
 65                  70                  75                  80
Val Pro Ala Leu His His Pro Val Phe Gln Gln Glu Ser Phe Thr Arg
                 85                  90                  95
Gln Val Leu Trp Lys Leu Leu Lys Val Val Lys Phe Gly Glu Val Ile
                100                 105                 110
Ser Tyr Gln Gln Leu Ala Ala Leu Ala Gly Asn Pro Ala Ala Thr Ala
                115                 120                 125
Ala Val Lys Thr Ala Leu Ser Gly Asn Pro Val Pro Ile Leu Ile Pro
                130                 135                 140
Cys His Arg Val Val Ser Ser Gly Ala Val Gly Tyr Glu Gly
145                 150                 155                 160
Gly Leu Ala Val Lys Glu Trp Leu Leu Ala His Glu Gly His Arg Leu
                165                 170                 175
Gly Lys Pro Gly Leu
            180

<210> SEQ ID NO 8
<211> LENGTH: 63
<212> TYPE: DNA
<213> ORGANISM: Artificial sequence
<220> FEATURE:
<223> OTHER INFORMATION: Ig-Kappa leader nucleotide sequence

<400> SEQUENCE: 8
atggagacag acacactcct gctatgggta ctgctgctct gggttccagg ttccactggt    60
gac                                                                  63

<210> SEQ ID NO 9
<211> LENGTH: 21
<212> TYPE: PRT
<213> ORGANISM: Artificial sequence
<220> FEATURE:
<223> OTHER INFORMATION: Ig-Kappa leader amino acid sequence

<400> SEQUENCE: 9

Met Glu Thr Asp Thr Leu Leu Leu Trp Val Leu Leu Leu Trp Val Pro
  1               5                  10                  15
Gly Ser Thr Gly Asp
            20

<210> SEQ ID NO 10
<211> LENGTH: 18
<212> TYPE: DNA
<213> ORGANISM: Artificial sequence
<220> FEATURE:
<223> OTHER INFORMATION: 6xHis tag nucleotide sequence

<400> SEQUENCE: 10
catcatcatc atcatcat                                                  18

<210> SEQ ID NO 11
<211> LENGTH: 6
<212> TYPE: PRT
<213> ORGANISM: Artificial sequence
<220> FEATURE:
<223> OTHER INFORMATION: 6xHis tag amino acid sequence
```

<400> SEQUENCE: 11

His His His His His His
1               5

<210> SEQ ID NO 12
<211> LENGTH: 15
<212> TYPE: DNA
<213> ORGANISM: Artificial sequence
<220> FEATURE:
<223> OTHER INFORMATION: Enterokinase cleavage site nucleotide sequence

<400> SEQUENCE: 12
gacgacgacg acaag                                                    15

<210> SEQ ID NO 13
<211> LENGTH: 5
<212> TYPE: PRT
<213> ORGANISM: Artificial sequence
<220> FEATURE:
<223> OTHER INFORMATION: Enterokinase cleavage site amino acid sequence

<400> SEQUENCE: 13

Asp Asp Asp Asp Lys
1               5

<210> SEQ ID NO 14
<211> LENGTH: 551
<212> TYPE: PRT
<213> ORGANISM: Artificial sequence
<220> FEATURE:
<223> OTHER INFORMATION: Second generation Annexin A5 SNAP polypeptide
      precursor amino acid sequence

<400> SEQUENCE: 14

Met Glu Thr Asp Thr Leu Leu Leu Trp Val Leu Leu Leu Trp Val Pro
1               5                   10                  15

Gly Ser Thr Gly Asp Ala Ala His His His His His His Ala Ala Asp
            20                  25                  30

Asp Asp Asp Lys Ala Ala Gln Pro Ala Ala Gln Val Leu Arg Gly Thr
        35                  40                  45

Val Thr Asp Phe Pro Gly Phe Asp Glu Arg Ala Asp Ala Glu Thr Leu
    50                  55                  60

Arg Lys Ala Met Lys Gly Leu Gly Thr Asp Glu Glu Ser Ile Leu Thr
65                  70                  75                  80

Leu Leu Thr Ser Arg Ser Asn Ala Gln Arg Gln Glu Ile Ser Ala Ala
                85                  90                  95

Phe Lys Thr Leu Phe Gly Arg Asp Leu Leu Asp Asp Leu Lys Ser Glu
            100                 105                 110

Leu Thr Gly Lys Phe Glu Lys Leu Ile Val Ala Leu Met Lys Pro Ser
        115                 120                 125

Arg Leu Tyr Asp Ala Tyr Glu Leu Lys His Ala Leu Lys Gly Ala Gly
    130                 135                 140

Thr Asn Glu Lys Val Leu Thr Glu Ile Ile Ala Ser Arg Thr Pro Glu
145                 150                 155                 160

Glu Leu Arg Ala Ile Lys Gln Val Tyr Glu Glu Tyr Gly Ser Ser
                165                 170                 175

Leu Glu Asp Asp Val Val Gly Asp Thr Ser Gly Tyr Tyr Gln Arg Met
            180                 185                 190

Leu Val Val Leu Leu Gln Ala Asn Arg Asp Pro Asp Ala Gly Ile Asp
        195                 200                 205

Glu Ala Gln Val Glu Gln Asp Ala Gln Ala Leu Phe Gln Ala Gly Glu
            210                 215                 220

Leu Lys Trp Gly Thr Asp Glu Lys Phe Thr Ile Phe Gly Thr
225                 230                 235                 240

Arg Ser Val Ser His Leu Arg Lys Val Phe Asp Lys Tyr Met Thr Ile
                245                 250                 255

Ser Gly Phe Gln Ile Glu Glu Thr Ile Asp Arg Glu Thr Ser Gly Asn
            260                 265                 270

Leu Glu Gln Leu Leu Leu Ala Val Val Lys Ser Ile Arg Ser Ile Pro
        275                 280                 285

Ala Tyr Leu Ala Glu Thr Leu Tyr Tyr Ala Met Lys Gly Ala Gly Thr
    290                 295                 300

Asp Asp His Thr Leu Ile Arg Val Met Val Ser Arg Ser Glu Ile Asp
305                 310                 315                 320

Leu Phe Asn Ile Arg Lys Glu Phe Arg Lys Asn Phe Ala Thr Ser Leu
                325                 330                 335

Tyr Ser Met Ile Lys Gly Asp Thr Ser Gly Asp Tyr Lys Lys Ala Leu
            340                 345                 350

Leu Leu Leu Cys Gly Glu Asp Ala Ala Ala Leu Glu Ser Arg Met
        355                 360                 365

Asp Lys Asp Cys Glu Met Lys Arg Thr Thr Leu Asp Ser Pro Leu Gly
370                 375                 380

Lys Leu Glu Leu Ser Gly Cys Glu Gln Gly Leu His Glu Ile Lys Leu
385                 390                 395                 400

Leu Gly Lys Gly Thr Ser Ala Ala Asp Ala Val Glu Val Pro Ala Pro
                405                 410                 415

Ala Ala Val Leu Gly Gly Pro Glu Pro Leu Met Gln Ala Thr Ala Trp
            420                 425                 430

Leu Asn Ala Tyr Phe His Gln Pro Glu Ala Ile Glu Glu Phe Pro Val
        435                 440                 445

Pro Ala Leu His His Pro Val Phe Gln Gln Glu Ser Phe Thr Arg Gln
    450                 455                 460

Val Leu Trp Lys Leu Leu Lys Val Val Lys Phe Gly Glu Val Ile Ser
465                 470                 475                 480

Tyr Gln Gln Leu Ala Ala Leu Ala Gly Asn Pro Ala Ala Thr Ala Ala
                485                 490                 495

Val Lys Thr Ala Leu Ser Gly Asn Pro Val Pro Ile Leu Ile Pro Cys
            500                 505                 510

His Arg Val Val Ser Ser Ser Gly Ala Val Gly Gly Tyr Glu Gly Gly
        515                 520                 525

Leu Ala Val Lys Glu Trp Leu Leu Ala His Glu Gly His Arg Leu Gly
    530                 535                 540

Lys Pro Gly Leu Ala Glu His
545                 550

<210> SEQ ID NO 15
<211> LENGTH: 1656
<212> TYPE: DNA
<213> ORGANISM: Artificial sequence
<220> FEATURE:
<223> OTHER INFORMATION: Second generation Annexin A5 SNAP polypeptide
      precursor nucleotide sequence

<400> SEQUENCE: 15
atggagacag acacactcct gctatgggta ctgctgctct gggttccagg ttccactggt        60

```
gacgccgccc atcatcatca tcatcatgcc gccgacgacg acgacaaggc ggcccagccg      120
gccgcacagg ttctcagagg cactgtgact gacttccctg gatttgatga gcgggctgat      180
gcagaaactc ttcggaaggc tatgaaaggc ttgggcacag atgaggagag catcctgact      240
ctgttgacat cccgaagtaa tgcccagcgc caggaaatct ctgcagcttt taagactctg      300
tttggcaggg atcttctgga tgacctgaaa tcagaactaa ctggaaaatt tgaaaaatta      360
attgtggctc tgatgaaacc ctctcggctt tatgatgctt atgaactgaa acatgccttg      420
aagggagctg gaacaaatga aaaagtactg acagaaatta ttgcttcaag gacacctgaa      480
gaactgagag ccatcaaaca agtttatgaa gaagaatatg gctcaagcct ggaagatgac      540
gtggtggggg acacttcagg gtactaccag cggatgttgg tggttctcct tcaggctaac      600
agagaccctg atgctggaat tgatgaagct caagttgaac aagatgctca ggctttattt      660
caggctggag aacttaaatg ggggacagat gaagaaaagt ttatcaccat ctttggaaca      720
cgaagtgtgt ctcatttgag aaaggtgttt gacaagtaca tgactatatc aggatttcaa      780
attgaggaaa ccattgaccg cgagacttct ggcaatttag agcaactact ccttgctgtt      840
gtgaaatcta ttcgaagtat acctgcctac cttgcagaga ccctctatta tgctatgaag      900
ggagctggga cagatgatca taccctcatc agagtcatgg tttccaggag tgagattgat      960
ctgtttaaca tcaggaagga gtttaggaag aattttgcca cctctctttta ttccatgatt     1020 aagggagata catctgggga ctataagaaa gctcttctgc tgctctgtgg agaagatgac     1080
gcggccgcac tcgagtctag aatggacaaa gactgcgaaa tgaagcgcac cacccctgga     1140
agccctctgg gcaagctgga actgtctggg tgcgaacagg gcctgcacga gatcaagctg     1200
ctgggcaaag gaacatctgc cgccgacgcc gtggaagtgc ctgccccagc cgccgtgctg     1260
ggcggaccag agccactgat gcaggccacc gcctggctca acgcctactt tcaccagcct     1320
gaggccatcg aggagttccc tgtgccagcc ctgcaccacc cagtgttcca gcaggagagc     1380
tttacccgcc aggtgctgtg gaaactgctg aaagtggtga gttcggaga ggtcatcagc      1440 taccagcagc tggcggccct ggcgggcaat cccgccgcca ccgccgccgt gaaaaccgcc     1500
ctgagcggaa atcccgtgcc cattctgatc ccctgccacc gggtggtgtc tagctctggc     1560
gccgtggggg gctacgaggg cgggctcgcc gtgaaagagt ggctgctggc ccacgagggc     1620
cacagactgg gcaagcctgg gctggctgag cactga                              1656
```

<210> SEQ ID NO 16
<211> LENGTH: 7
<212> TYPE: PRT
<213> ORGANISM: Artificial sequence
<220> FEATURE:
<223> OTHER INFORMATION: Second Generation Linker Peptide

<400> SEQUENCE: 16

Ala Ala Ala Leu Glu Ser Arg
1               5

FUSION PROTEINS FOR THE DETECTION OF APOPTOSIS

PRIORITY AND CROSS REFERENCE TO RELATED APPLICATIONS

This application is the U.S. National Stage Application under 35 U.S.C. § 371 of International Application No. PCT/IB2018/059704, filed Dec. 6, 2018, designating the U.S. and published in English as WO 2019/111194 A1 on Jun. 13, 2019, which claims the benefit of Great Britain Patent Application No. GB 1720358.9, filed Dec. 6, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled SPR004001APCSEQLIST.txt, created and last modified on Jun. 4, 2020, which is 27,700 bytesin size. The information in the Electronic Sequence Listing is incorporated herein by reference in its entirety.

BACKGROUND OF THE INVENTION

The present invention relates to fusion proteins which are capable of binding to phosphatidylserine, comprising a modified $O^6$-alkylguanine-DNA alkyltransferase which is capable of autoconjugation to an $O^6$-benzylguanine-modified label, the fusion proteins being capable of detecting apoptosis in a cell population. The invention also relates to recombinant polypeptide precursors which comprise a secretion leader sequence, purification tag, protease cleavage site and the fusion protein. Also included in the scope of the invention are nucleic acids encoding the recombinant polypeptide precursor, vectors comprising the nucleic acids, host cells comprising the vectors, methods of production of the fusion proteins, kits and assays for detecting apoptosis.

Apoptosis, also termed programmed cell death, is a natural process used by cells to self-destruct and control aberrant growth. To date, scientists have continued to seek more insight in order to understand the complexity of the cellular events that occur when cells undergo apoptosis. The field of drug discovery has also witnessed development of therapies that seek to eliminate diseased cell populations by selectively driving target cells into apoptosis. In both cases, availability of tools that allow for the specific detection and study of apoptotic cell populations are important.

Annexin A5 (or annexin V) is a cellular protein in the annexin group and is commonly used in flow cytometry to detect apoptotic cells by its ability to bind to phosphatidylserine. Phosphatidylserine acts as a marker of apoptosis when it occurs on the outer surface of the plasma membrane of a cell. Annexin A5 has been proposed to play a role in the inhibition of blood coagulation by competing for phosphatidylserine binding sites with prothrombin and also to inhibit the activity of phospholipase A1. These properties have been found by in vitro experiments.

The use of Annexin A5 (36-kDa) as a ligand that specifically binds phosphatidylserine residues on the surface of cells undergoing apoptosis remains one of the most popular methods of detection of apoptosis. This is possible because in normal cells phosphatidylserine residues are restricted to the inner layer of the cell membrane where they contribute to intracellular signalling. On the other hand, when cells undergo apoptosis, phosphatidylserine is flipped and exposed to the outer surface of the cell membrane where it plays a role in the recognition of apoptotic cells by phagocytes, such as macrophages and dendritic cells. The presence of phosphatidylserine on the cell surface is a clear indication of apoptosis and the ability of Annexin A5 to bind to phosphatidylserine is useful for the in vitro or ex vivo detection of apoptosis. Because, annexin A5 binds to phosphatidylserine with high affinity; fluorescently labelled Annexin V can be used to detect phosphatidylserine that is exposed on the outside of apoptotic cells.

Previously several types of Annexin A5-fluorescent probes have been developed and are readily available commercially from different vendors. Most of these probes have been optimized for molecular imaging and are delivered in the form of an easy to use kit. Most of the commercially available annexin A5-fluorescent probes are prepared by chemical modification and conjugation strategies, which have several limitations. For example, one method relies on the coupling of fluorophores to annexin A5 via the lysine side chains of the annexin A5 protein using amine-reactive fluorophores. This approach has several drawbacks which includes heterogeneous annexin A5 conjugated products as a result of inability to control the number of bound fluorophores. In addition, in some instances fluorescence quenching may occur as a result of multiple fluorophores binding to annexin A5 in close proximity to each other. A further, drawback of the chemical conjugation approach is that the conjugation of fluorophores to freely accessible lysine residues may occur in the active binding site of the ligand which inhibits the ability of annexin A5 to bind to phosphatidylserine.

Other approaches which have sought to solve the above-mentioned shortcomings of chemical conjugation include the genetic fusion of annexin A5 to fluorescent proteins such as eGFP. This approach has resulted in functional proteins being produced but the protein products also suffer from several limitations, including high background noise, irradiation with other dyes and the high cost of production of each different annexin A5-fluorophore colour or wavelength.

The present invention is aimed at overcoming the difficulties experienced with chemically conjugating dyes to annexin A5 and/or using non-specific fluorescent proteins.

SUMMARY OF THE INVENTION

The present invention relates to fusion proteins which are capable of binding to phosphatidylserine comprising a modified $O^6$-alkylguanine-DNA alkyltransferase which is capable of autoconjugation to an $O^6$-benzylguanine-modified label, the fusion proteins being capable of detecting apoptosis in a cell population.

According to a first aspect of the invention there is provided for a recombinant polypeptide precursor, comprising the following formula:

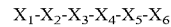

wherein, $X_1$ is a secretion leader sequence, $X_2$ is a purification tag, $X_3$ is a protease cleavage site, $X_4$ is a phosphatidylserine binding ligand, $X_5$ is a peptide linker comprising the amino acid sequence AAALESR (SEQ ID NO:16); and $X_6$ is a modified $O^6$-alkylguanine-DNA alkyltransferase, wherein the enterokinase cleavage site facilitates the cleavage of $X_4$-$X_5$-$X_6$ from the recombinant polypeptide precursor to produce a mature recombinant polypeptide capable of binding to phosphatidylserine; and further wherein $X_6$ is capable of autoconjugation to an $O^6$-benzylguanine-modified label.

In one embodiment of the invention the phosphatidylserine binding ligand may be any amino acid sequence that facilitates binding of the fusion protein to a cell which presents phosphatidylserine on its surface. Preferably, the phosphatidylserine binding ligand is Annexin A5.

In one embodiment of the invention the secretion leader sequence may be an amino acid sequence that facilitates the secretion of a polypeptide of interest from a cell. Those of skill in the art will appreciate that non-limiting examples of typical secretion leader sequences may include mammalian, murine and prokaryotic signal peptide, human placental secretory alkaline phosphatase (SEAP), interleukin-2, CD5, Immunoglobulin Kappa light chain, trypsinogen, serum albumin, prolactin or CD33 leader sequence. Preferably, the secretion leader sequence is an IgK leader sequence.

In another embodiment of the invention the purification tag may be any amino acid sequence that facilitates the purification of a polypeptide of interest. Those of skill in the art will appreciate that non-limiting examples of typical purification tags may include poly-histidine, glutathione S-transferase, maltose binding protein, calmodulin binding peptide, streptavidin or biotin-based tags, HALO tag, FLAG tag thioredoxin-tag, AviTag, Myc-tag, NE-tag, green fluorescent protein-tag, polyglutamate tag etc. Preferably, the purification tag is a poly histidine sequence and most preferably the purification tag is a 6x-His sequence.

In yet a further embodiment of the invention the protease cleavage site may be any amino acid sequence that is capable of being cleaved by a proteolytic enzyme. Those of skill in the art will appreciate that non-limiting examples of typical protease enzymes may include an enterokinase, caspase-1, caspase-2, caspase-3, caspase-4, caspase-5, caspase-6, caspase-7, caspase-8, caspase-9, caspase-1 0, factor Xa, granzyme B, HRV3C protease, TEV protease and thrombin. Preferably, the protease cleavage site is an enterokinase cleavage site.

In a preferred embodiment of the invention the $O^6$-alkylguanine-DNA alkyltransferase is an $O^6$-methylguanine-DNA methyltransferase. In yet a further embodiment of the invention the $O^6$-benzylguanine-modified label is selected from the group consisting of $O^6$-benzylguanine modified with an label such as Alexa Fluor 488, Alexa Fluor 633, Allophycocyanin (APC), APC-Cy7, Carboxyfluorescein Diacetate (CFSE), Cy3, Cy5, Fluorescein isothiocyanate (FITC), Peridinin chlorophyll protein (PerCP), Phycoerythrin (PE or R-PE), Phycoerythrin-Cy5, Phycoerythrin-Texas Red (PE-Texas Red) and Texas Red. Those of skill in the art will however appreciate that this is a non-exhaustive list of possible labels.

In a most preferred embodiment of the invention the recombinant polypeptide precursor comprises a sequence of SEQ ID NO:14.

According to a second aspect of the invention provides for nucleic acid molecules encoding the recombinant polypeptide precursor of the invention. In some embodiments, the nucleic acid molecules of the invention may be operably linked to regulatory sequences in such a way as to permit gene expression thereof when the appropriate molecules are bound to the regulatory sequences. Such operably linked sequences may be in the form of vectors or expression constructs that can be transformed or transfected into host cells for expression. It will be appreciated by those of skill in the art that any suitable vector can be used for this purpose. Further it will be appreciated that any suitable expression system may be used, expression systems include host cells transformed with the expression vectors and may include bacterial cells, yeast cells, insect cells, plant cells and/or mammalian cells.

In a preferred embodiment of this aspect of the invention the nucleic acid molecule encodes a recombinant polypeptide precursor comprising a sequence of SEQ ID NO:14.

It will also be appreciated that expression vectors which comprise the nucleic acid molecules encoding the recombinant polypeptide precursors and expression cassettes comprising the nucleic acid molecules encoding the recombinant polypeptide precursors also fall within the scope of an embodiment of the invention.

In a third aspect of the invention there is provided for a method for producing a mature recombinant polypeptide capable of binding to phosphatidylserine, the method comprising the steps of:

(i) providing an expression vector comprising a nucleic acid molecule encoding a recombinant polypeptide precursor having the formula $X_1$-$X_2$-$X_3$-$X_4$-$X_5$-$X_6$, wherein $X_1$ is a secretion leader sequence, $X_2$ is a purification tag, $X_3$ is protease cleavage site, $X_4$ is a phosphatidylserine binding ligand, $X_5$ is a peptide linker comprising the amino acid sequence AAALESR (SEQ ID NO:16); and $X_6$ is a modified $O^6$-alkylguanine-DNA alkyltransferase;

(ii) transfecting a host cell with the expression vector of step (i);

(iii) expressing the recombinant polypeptide precursor by the host cell in a cell culture medium;

(iv) secreting the recombinant polypeptide precursor from the host cell into the supernatant of the cell culture medium using the secretion leader sequence;

(v) recovering the recombinant polypeptide precursor from the supernatant using the purification tag;

(vi) cleaving the recombinant polypeptide precursor with a protease to produce the mature recombinant polypeptide, wherein the mature polypeptide comprises $X_4$-$X_5$-$X_6$ of the recombinant polypeptide precursor; and (vii) autoconjugating an $O^6$-benzylguanine-modified label to $X_6$.

In a preferred embodiment of the invention the invention the host cell is a HEK293T cell.

In one embodiment of the invention the recombinant polypeptide precursor is recovered from the supernatant by affinity chromatography.

In a fourth aspect of the invention there is provided for a mature recombinant polypeptide capable of binding to phosphatidylserine, produced according to the methods set out herein.

A fifth embodiment of the invention provides for a kit comprising the mature recombinant polypeptide of the invention and instructions for its use.

In a sixth embodiment of the invention there is provided for an assay for detecting apoptosis in a cell population from a subject, the assay comprising the steps of:

(i) contacting the cell population with the mature recombinant polypeptide of the invention; and (ii) detecting the binding of the phosphatidylserine binding ligand to phosphatidylserine on the cell surface, wherein binding of the ligand is indicative of apoptosis in the cell population. It will be appreciated by those of skill in the art that the step of detection of binding of the mature recombinant polypeptide to phosphatidylserine in the cell population is performed by detecting the presence of the $O^6$-benzylguanine-modified label

BRIEF DESCRIPTION OF THE DRAWINGS

Non-limiting embodiments of the invention will now be described by way of example only and with reference to the following figures:

FIG. 1: Plasmid map of constructed Annexin A5-SNAP pMS Vector. The eGFP protein is expressed as a reporter protein under the control of an IRES sequence.

FIG. 2: Amino acid sequence of a first generation construct of the invention (SEQ ID NO:1) comprising IgKappa, poly-His tag, enterokinase cleavage site, Annexin AV and SNAP-tag. IgK is a leader sequence helping this protein to be excreted from the producing cells, poly-His tag allows for purification of the protein via immobilized metal affinity chromatography, the enterokinase cleavage site allows removal of the N-terminal tag.

FIG. 4: Nucleic acid sequence encoding the first generation recombinant polypeptide precursor (SEQ ID NO:2).

FIG. 5: Amino acid sequence of the mature recombinant polypeptide (SEQ ID NO:3).

FIG. 6: Nucleic acid sequence of the annexin A5 ORF modified with SfiI and NotI restriction sites (SEQ ID NO:4).

FIG. 7: Amino acid sequence of the annexin A5 protein (SEQ ID NO:5).

FIG. 8: Nucleic acid sequence of the SNAP-tag (SEQ ID NO:6).

FIG. 9: Amino acid sequence of the SNAP-tag (SEQ ID NO:7).

FIG. 10: Amino acid sequence of the construct of the invention (SEQ ID NO:14) comprising IgKappa, poly-His tag, enterokinase cleavage site, Annexin AV and SNAP-tag. IgK is a leader sequence helping this protein to be excreted from the producing cells, poly-His tag allows for purification of the protein via immobilized metal affinity chromatography, the enterokinase cleavage site allows removal of the N-terminal tag.

FIG. 11: Nucleic acid sequence encoding the recombinant polypeptide precursor (SEQ ID NO:15).

SEQUENCE LISTING

Figure 3:
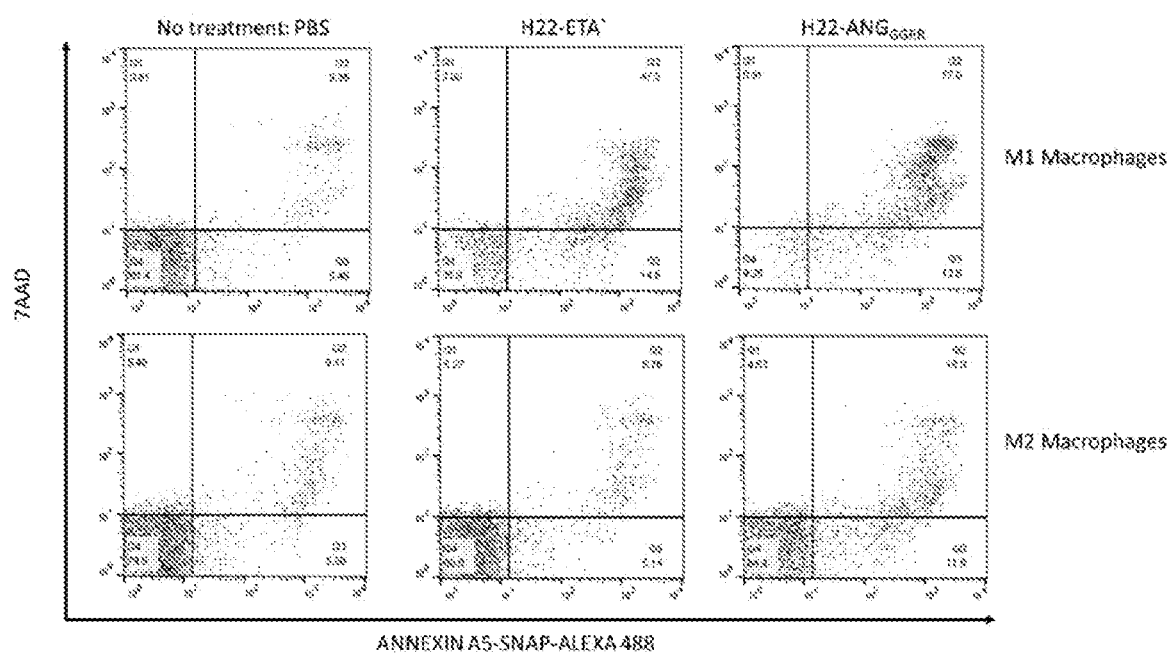
FIG. 3: Flow cytometry analysis of selective elimination of M1-polarized macrophages in vitro.

The nucleic acid and amino acid sequences listed in the accompanying sequence listing are shown using standard letter abbreviations for nucleotide bases, and the standard three letter abbreviations for amino acids. It will be understood by those of skill in the art that only one strand of each nucleic acid sequence is shown, but that the complementary strand is included by any reference to the displayed strand. In the accompanying sequence listing:

SEQ ID NO:1—Amino acid sequence of a first generation construct of the recombinant polypeptide precursor comprising Ig-Kappa, poly-His tag, enterokinase cleavage site, Annexin AV and SNAP-tag fusion protein.

SEQ ID NO:2—Nucleic acid sequence encoding the first generation construct of the recombinant polypeptide precursor comprising Ig-Kappa, 6x His-tag, enterokinase cleavage site, Annexin AV and SNAP-tag construct.

SEQ ID NO:3—Amino acid sequence of the mature first generation recombinant polypeptide comprising the Annexin AV-SNAP-tag cleavage product.

SEQ ID NO:4—Nucleic acid sequence of the annexin A5 ORF modified with SfiI and NotI restriction sites.

SEQ ID NO:5—Amino acid sequence of the annexin A5 protein.

SEQ ID NO:6—Nucleic acid sequence of the SNAP-tag.

SEQ ID NO:7—Amino acid sequence of the SNAP-tag.

SEQ ID NO:8—Nucleic acid sequence of the Ig-Kappa leader sequence.

SEQ ID NO:9—Amino acid sequence of the Ig-Kappa leader sequence.

SEQ ID NO:10—Nucleic acid sequence of the 6xHis tag.

SEQ ID NO:11—Amino acid sequence of the 6xHis tag.

SEQ ID NO:12—Nucleic acid sequence of the enterokinase cleavage site.

SEQ ID NO:13—Amino acid sequence of the enterokinase cleavage site.

SEQ ID NO:14—Amino acid sequence of the second generation recombinant polypeptide precursor comprising Ig-Kappa, poly-His tag, enterokinase cleavage site, Annexin AV, AAASLR peptide linker and SNAP-tag fusion protein.

SEQ ID NO:15—Nucleic acid sequence encoding the second generation recombinant polypeptide precursor comprising Ig-Kappa, 6x His-tag, enterokinase cleavage site, Annexin AV, AAASLR peptide linker and SNAP-tag construct.

SEQ ID NO:16—Amino acid sequence of the peptide linker.

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms "a", "an" and "the" include the plural form, unless the context clearly indicates otherwise.

The terminology and phraseology used herein is for the purpose of description and should not be regarded as limiting. The use of the terms "comprising", "containing", "having" and "including" and variations thereof used herein, are meant to encompass the items listed thereafter and equivalents thereof as well as additional items.

Once a cell commences with the process of apoptosis it exposes phosphatidylserine (PS) on its surface. Annexin A5 is a ligand which specifically binds to phosphatidylserine on the surface of a cell. The present inventors have developed a SNAP tag based fusion protein for the selective detection of phosphatidylserine on the surface of a cell. The present invention has a distinct advantage in comparison to the previously described state of the art annexin A5 detection molecules.

The present invention has several major differences between the previously described chemically modified annexin A5-fluorescent probes and/or annexin A5-eGFP proteins, these include:

1. The use of a SNAP-tag as a labelling tag which allows for simple site-specific conjugation of any BG-modified fluorophore and a 1:1 stoichiometric conjugation ratio of the BG-modified fluorophore to annexin A5. The ability of being able to conjugate any BG-modified fluorophore to the fusion protein of the invention will result in a substantially lower cost for the preparation of a panel of annexin A5 detection fluorochromes, together with the ability to produce reproducible results.

2. The covalent SNAP-tag labelling reaction is an auto-conjugation event which is occurs under physiological conditions and which does not require enzymatic attachment or acidic or alkaline media to facilitate attachment of the fluorophore which can be deleterious to the functional properties of either the protein or fluorophore.

3. The currently commercially available annexin A5-fluorophore products are not recommended for use in the detection of apoptotic adherent cells. The present inventors have however shown that optimal results are obtained for the use of Annexin A5-SNAP conjugated to different fluorophores including Alexa 488, Alexa 449, and Alexa 649 in the detection of apoptotic macrophages. This shows the versatility of the annexin A5-SNAP protein of the invention as tool for the detection of apoptosis across all cell types.

The present invention relates to the development of an Annexin A5-SNAP fusion protein with robust function in targeting phosphatidylserine on the surface of cells undergoing apoptosis. The inventors have demonstrated the use and ability of annexin A5-SNAP coupled to a detectable label to monitor induction of apoptosis on cells by identifying the selective killing of M1 macrophages by *Pseudomonas* exotoxin A-based recombinant immunotoxins and Angiogenin based human cytolytic fusion proteins.

These detectable labels may include one of the following SNAP-Cell® Oregon Green®, SNAP-Cell® TMR-Star, SNAP-Cell® 430, SNAP-Cell® 647-SiR, SNAP-Surface® 488, SNAP-Surface® 549, SNAP-Surface® 594, SNAP-Surface® 649, SNAP-Surface® Alexa Fluor® 488, SNAP-Surface® Alexa Fluor® 546, SNAP-Surface® Alexa Fluor® 647, SNAP-Vista® Green.

Preferably the detectable label may be an $O^6$-benzylguanine-modified label selected from the group consisting of Alexa Fluor 488, Alexa Fluor 633, Allophycocyanin (APC), APC-Cy7, Carboxyfluorescein Diacetate (CFSE), Cy3, Cy5, Fluorescein isothiocyanate (FITC), Peridinin chlorophyll protein (PerCP), Phycoerythrin (PE or R-PE), Phycoerythrin-Cy5, Phycoerythrin-Texas Red (PE-Texas Red, also written Texas Red-PE) and Texas Red.

The present invention specifically relates to a phosphatidylserine-binding ligand, preferably annexin A5 fusion protein recombinantly fused to a SNAP tag and separated by an amino acid linker. In a preferably embodiment the fusion protein comprises an lgk leader sequence, a poly-His tag purification tag, and a protease cleavage site, preferably the protease cleavage site is an enterokinase cleavage site (SEQ ID NO:14), hereinafter referred to as the fusion protein of the invention.

A "protein," "peptide" or "polypeptide" is any chain of two or more amino acids, including naturally occurring or non-naturally occurring amino acids or amino acid analogues, irrespective of post-translational modification (e.g., glycosylation or phosphorylation).

The terms "nucleic acid" or "nucleic acid molecule" encompass both ribonucelotides (RNA) and deoxyribonucleotides (DNA), including cDNA, genomic DNA, and synthetic DNA. The nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. By "RNA" is meant a sequence of two or more covalently bonded, naturally occurring or modified ribonucleotides. The term "DNA" refers to a sequence of two or more covalently bonded, naturally occurring or modified deoxyribonucleotides. By "cDNA" is meant a complementary or copy DNA produced from an RNA template by the action of RNA-dependent DNA polymerase (reverse transcriptase).

Accordingly, a "cDNA clone" refers to a duplex DNA sequence which is complementary to an RNA molecule of interest, and which is carried in a cloning vector. The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

In some embodiments, a fusion protein of the invention may include, without limitation, a fusion polypeptide including an amino acid sequence substantially identical to the amino acid sequence a fusion protein comprising a secretion leader sequence, a purification tag, a protease cleavage site, a phosphatidylserine-binding ligand and a SNAP tag or a derivative thereof. In a preferred embodiment of the invention the fusion protein comprises a secretion leader sequence which is an lgk or a derivative thereof, the purification tag is a poly-His tag, the protease cleavage site is an enterokinase cleavage site or a derivative thereof, the phosphatidylserine-binding ligand is annexin A5 or a derivative thereof and a SNAP tag or a derivative thereof. Preferably, the fusion protein of the invention comprises SEQ ID NO:14. Another embodiment of the invention includes, without limitation, nucleic acid molecules encoding the aforementioned fusion protein. A further embodiment of the invention comprises a derivative of the fusion protein of the invention comprising annexin A5 fused to a SNAP-tag after the lgk leader sequence which facilitates excretion of the fusion protein from the cells in which it is produced, the 6xHis tag which facilitates purification of the fusion protein via immobilized metal affinity chromatography and the enterokinase cleavage site which allows removal of the N-terminal tag have been cleaved from each other at the enterokinase cleavage site.

The term "isolated", is used herein and means having been removed from its natural environment.

The term "poly-His tag", as used herein refers to a linear sequence of histidine residues allowing for the purification of a recombinant protein by metal chelate affinity chromatography. Alternatively, a poly-His tag may be used to detect a recombinant polypeptide using an anti-poly-His tag antibody. A poly-His tag may comprise 6, 7, 8, 9 or 10 consecutive Histidine residues.

The term "purified", relates to the isolation of a molecule or compound in a form that is substantially free of contamination or contaminants. Contaminants are normally associated with the molecule or compound in a natural environment, purified thus means having an increase in purity as a result of being separated from the other components of an original composition. The term "purified nucleic acid" describes a nucleic acid sequence that has been separated from other compounds including, but not limited to polypeptides, lipids and carbohydrates which it is ordinarily associated with in its natural state.

The term "complementary" refers to two nucleic acid molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of the expressed fusion protein or of the polypeptide encoded by the nucleic acid molecule. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80% sequence identity, at least about 90% sequence identity, or even greater sequence identity, such as about 95%, about 96%, about 97%, about 98% or about 99% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

In an alternative embodiment of the invention, the fusion proteins of the invention may be prepared by, for instance, inserting, deleting or replacing amino acid residues at any position of the polypeptide sequences and/or, for instance inserting, deleting or replacing nucleic acids at any position of the nucleic acid molecule encoding the fusion protein of the invention.

Those skilled in the art will appreciate that polypeptides, peptides or peptide analogues can be synthesised using standard chemical techniques, for instance, by automated synthesis using solution or solid phase synthesis methodology. Automated peptide synthesisers are commercially available and use techniques known in the art. Polypeptides, peptides and peptide analogues can also be prepared from their corresponding nucleic acid molecules using recombinant DNA technology.

In some embodiments, the nucleic acid molecules of the invention may be operably linked to other sequences. By "operably linked" is meant that the nucleic acid molecules encoding the fusion proteins of the invention and regulatory sequences are connected in such a way as to permit expression of the fusion proteins when the appropriate molecules are bound to the regulatory sequences. Such operably linked sequences may be contained in vectors or expression constructs which can be transformed or transfected into host cells for expression. It will be appreciated that any vector can be used for the purposes of expressing the fusion proteins of the invention.

As used herein, the term "gene" refers to a nucleic acid that encodes a functional product, for instance a RNA, polypeptide or protein. A gene may include regulatory sequences upstream or downstream of the sequence encoding the functional product.

As used herein, the term "coding sequence" refers to a nucleic acid sequence that encodes a specific amino acid sequence. On the other hand a "regulatory sequence" refers to a nucleotide sequence located either upstream, downstream or within a coding sequence. Generally regulatory sequences influence the transcription, RNA processing or stability, or translation of an associated coding sequence. Regulatory sequences include but are not limited to: effector binding sites, enhancers, introns, polyadenylation recognition sequences, promoters, RNA processing sites, stem-loop structures, translation leader sequences and the like.

The term "promoter" refers to a DNA sequence that is capable of controlling the expression of a nucleic acid coding sequence or functional RNA. A promoter may be based entirely on a native gene or it may be comprised of different elements from different promoters found in nature or a promoter could be an entirely synthetic construct. Different promoters are capable of directing the expression of a gene in different cell types, or at different stages of development, or in response to different environmental or physiological conditions. A "constitutive promoter" is a promoter that directs the expression of a gene of interest in most host cell types most of the time.

The term "recombinant" means that something has been recombined. When used with reference to a nucleic acid construct the term refers to a molecule that comprises nucleic acid sequences that are joined together or produced by means of molecular biological techniques. The term "recombinant" when used in reference to a protein or a polypeptide refers to a protein or polypeptide molecule which is expressed from a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation. Such recombinant nucleic acid constructs may include sequences derived from the same host cell species or from different host cell species.

As used herein, the term "chimaeric", means that a sequence comprises of sequences that have been "recombined". By way of example sequences are recombined and are not found together in nature. The term "recombine" or "recombination" refers to any method of joining two or more polynucleotides. The term includes end to end joining, and insertion of one sequence into another. The term is intended to include physical joining techniques, for instance, sticky-end ligation, blunt-end ligation, as well as PCR-mediated fusion by overlap extension PCR. Sequences may also be artificially synthesized to contain a recombined sequence. The term may also encompass the integration of one sequence into a second sequence by way of, for example, homologous recombination.

The term "vector" refers to a means by which polynucleotides or gene sequences can be introduced into a cell. There are various types of vectors known in the art including plasmids, viruses, bacteriophages and cosmids. Generally polynucleotides or gene sequences are introduced into a vector by means of a cassette. The term "cassette" refers to a polynucleotide or gene sequence that is expressed from a vector, for example, the polynucleotide or gene sequences encoding the fusion proteins of the invention. A cassette generally comprises a gene sequence inserted into a vector, which in some embodiments, provides regulatory sequences for expressing the polynucleotide or gene sequences. In other embodiments, the vector provides the regulatory sequences for the expression of the fusion protein. In further embodiments, the vector provides some regulatory sequences and the nucleotide or gene sequence provides other regulatory sequences. "Regulatory sequences" include but are not limited to promoters, transcription termination sequences, enhancers, splice acceptors, donor sequences, introns, ribosome binding sequences, poly(A) addition sequences, and/or origins of replication.

In some embodiments, the fusion proteins or compositions according to the invention may be provided in a kit, together with instructions for use.

A major advantage of the present invention is the auto-conjugation of any label under physiological conditions needed for specific detection of an interaction of the fusion protein of the invention with apoptotic cells. The biology can be adjusted and is not restricted to a fluorophore of a precast wavelength being attached to annexin A5.

The following example is offered by way of illustration and not by way of limitation.

EXAMPLE 1

Generation of Annexin A5-SNAP

The open reading frame (ORF) for annexin A5 (SEQ ID NO:5) was modified with 5'-SfiI and 3'-NotI restriction sites in-silico and synthesized by Genescript (NJ, USA) (SEQ ID NO:4). The synthesized ORF was ligated into a SfiI/NotI-linearized pMS vector already containing the SNAP-tag sequence (FIG. 1) (SEQ ID NO:6). An Ig-Kappa leader sequence ((METDTLLLWVLLLWVPGSTGD (SEQ ID NO:9) encoded by the nucleic acid sequence ATGGAGACAG ACACACTCCT GCTATGGGTA CTGCTGCTCT GGGTTCCAGG TTCCACTGGT GAC (SEQ ID NO:8)) was introduced at the N-terminal of the fusion construct to allow secretion of the protein into the culture media. A 6x Histidine tag (HHHHHH (SEQ ID NO:11) encoded by the nucleic acid sequence CATCATCATC ATCATCAT (SEQ ID NO:10)) was also introduced to allow purification of the protein by immobilized metal ion affinity chromatography. An enterokinase cleavage site (DDDDK (SEQ ID NO:13) encoded by the nucleic acid sequence GACGACGACG ACAAG (SEQ ID NO:12)) was also introduced to allow separation of Annexin A5-SNAP from its N-terminal tags (SEQ ID NO:12) and a peptide linker (AAALESR (SEQ ID NO:16) was introduced in order to functionalise the mature recombinant polypeptide. Successful cloning was confirmed by sequencing.

Expression and Purification of Annexin A5-SNAP

Once molecular cloning was confirmed by sequencing, the pMS expression vector was used for the transfection of HEK293T cells (ATCC, Wesel, Germany, CRL-11268) using X-tremeGENE™ HP DNA Transfection Reagent (Roche, Germany) according to the manufacturer's instructions. For selection of successfully transfected cells, the culture medium was supplemented with Zeocin (Invitrogen, Carlsbad) 100 ng/mL. The recombinant proteins were purified from the cell culture supernatant by immobilized metal ion affinity chromatography using a 5 mL $Ni^{2+}$-NTA Superflow cartridge on an AKTA purifier system). Elution fractions were pooled and concentrated using 10 kDa Amicon Ultracentrifugation filters (Millipore, Germany). Protein concentration was estimated by nanodrop reading and structural integrity confirmed by SDS-PAGE and Coomassie Brilliant Blue staining. The inventors found that a first generation fusion protein comprising a linker sequence of AAASR only resulted in minor binding in the supernatant of the fusion protein. Additionally, it was found that the first generation fusion protein did not bind to the eluate. As a result the first generation fusion protein could not be used in a functional apoptosis assay. On the other hand a second generation fusion protein comprising a linker sequence of AAALESR (SEQ ID NO:16) worked surprisingly well and provided a mature fusion protein that could be used in functional apoptosis assays.

Labelling of Annexin A5-SNAP with BG-Modified Fluorophore

The labelling of purified annexin A5-SNAP with BG-Alexa 488 (Cat no: S9129S; New England Biolabs; NEB, Ipswich, Mass., USA) was carried out using 1.5-fold molar excess of dye to protein. Coupling was performed for 30 mins at 37° C. Successful coupling and fluorescence of labelled proteins was confirmed by SDS-PAGE and detection with a dark reader blue light transilluminator (Clare Chemical, Colorado, United States, MA, USA).

Preparation of and Treatment of Ex Vivo Differentiated Macrophages with RIT and hCFPs Human PBMCs were isolated from buffy coats by gradient centrifugation with lymphroprep (Alere Technologies, Norway) and cultured for 3 hours at a density of $10 \times 10^6$ cells/well in serum free media to select for monocytes by adherence. After which each well was subsequently washed with 1 ml of PBS (Sigma-Aldrich, Germany) to remove non-adherent cells. Polarization was carried out for 72 hours using 100 U/ml human IFN-γ (Sigma-Aldrich, Germany) and 1 µg/ml LPS (Sigma-Aldrich, Germany) for M1 and 20 ng/ml human IL-4 (Peprotech, Germany) for M2 macrophages. After 72 hours, the polarization was boosted with 50 U/ml human IFN-γ (Sigma-Aldrich, Germany) and 0.5 µg/ml LPS (Sigma-Aldrich, Germany) for M1 and 10 ng/ml human IL-4 (Peprotech, Germany) for M2 macrophage for additional 24 hours, after which macrophages were used for functional assays. The selective killing of M1 macrophages was demonstrated by treating cells with 200 nM concentration of H22(scFv)-ANG$_{GGRR}$ and 100 nM OF H22(scFv)-ETA for 24 hours. Negative control cells were treated with 30 mL PBS.

Apoptosis Assays

After 24 hours of treatment, selective induction of apoptosis in M1 IFN-Y/LPS polarized macrophages was measured by annexin A5/7-AAD staining. Briefly, cells were washed with 1 ML of PBS and lifted by incubating in 500 µl of Accutase (Sigma, Germany) for 10 mins. The cells were washed once with PBS and again with 1× annexin A5 binding buffer containing 10 mM HEPES, 140 mM NaCl, and 2.5 mM CaCl$_2$ (pH 7.4). Afterwards, cells were resuspended in 200 µl of 1× annexin A5 binding buffer and stained with 1.5 µg of annexin A5-SNAP-BG-Alexa 488 protein for 30 minutes. Cells were then washed with 1 ml 1× binding buffer and resuspended in 400 µl of 1× binding buffer including 7-AAD (1/1000 dilution).

Use of Annexin A5-SNAP-Alexa-488 for the Measurement of Apoptosis Induction in M1 and M2 Macrophages Specific and selective induction of apoptosis by anti-CD64 based RIT and hCFP was analysed by flow cytometry after staining of phosphatidylserine residues on the surface of apoptotic cells with annexin V5-SNAP-Alexa 488. As depicted in FIG. 3, treatment with H22(scFv)-ETA and H22-ANG(scFv)$_{GGRR}$ shows selectively killing of M1 polarized macrophages after 24 hours.

What is claimed is:

1. A recombinant polypeptide precursor, comprising the following formula:

$X_1$-$X_2$-$X_3$-$X_4$-$X_5$-$X_6$ wherein,
$X_1$ is a secretion leader sequence;
$X_2$ is a purification tag;
$X_3$ is a protease cleavage site;
$X_4$ is annexin A5;
$X_5$ is a peptide linker comprising the amino acid sequence AAALESR (SEQ ID NO:16); and
$X_6$ is a modified $O^6$-alkylguanine-DNA alkyltransferase;
wherein the protease cleavage site facilitates the cleavage of $X_4$-$X_5$-$X_6$ from the recombinant polypeptide precursor to produce a mature recombinant polypeptide capable of binding to phosphatidylserine; and wherein $X_6$ is capable of autoconjugation to an $O^6$-benzylguanine-modified label.

2. The recombinant polypeptide precursor of claim 1, wherein the secretion leader sequence is an Igk leader sequence.

3. The recombinant polypeptide precursor of claim 1, wherein the purification tag is a poly histidine tag.

4. The recombinant polypeptide precursor of claim 1, wherein the protease cleavage site is an enterokinase cleavage site.

5. The recombinant polypeptide precursor of claim 1, wherein the modified $O^6$-alkylguanine-DNA alkyltransferase is $O^6$-methylguanine-DNA methyltransferase.

6. The recombinant polypeptide precursor of claim 1, wherein the $O^6$-benzylguanine-modified label is selected from the group consisting of Alexa Fluor 488, Alexa Fluor 633, Allophycocyanin (APC), APC-Cy7, Carboxyfluorescein Diacetate (CFSE), Cy3, Cy5, Fluorescein isothiocyanate (FITC), Peridinin chlorophyll protein (PerCP), Phycoerythrin (PE or R-PE), Phycoerythrin-Cy5, Phycoerythrin-Texas Red (PE-Texas Red) and Texas Red.

7. The recombinant polypeptide precursor of claim 1, comprising the sequence of SEQ ID NO: 14.

8. A nucleic acid molecule encoding a recombinant polypeptide precursor of SEQ ID NO: 14.

9. An expression vector comprising the nucleic acid molecule of claim 8.

10. A host cell transformed with the vector of claim 9.

11. A method for producing a mature recombinant polypeptide capable of binding to phosphatidylserine, the method comprising the steps of:
(i) providing an expression vector comprising a nucleic acid molecule encoding a recombinant polypeptide precursor having the formula:

$X_1$-$X_2$-$X_3$-$X_4$-$X_5$-$X_6$ wherein,
$X_1$ is a secretion leader sequence;
$X_2$ is a purification tag;
$X_3$ is protease cleavage site;
$X_4$ is annexin A5;
$X_5$ is a peptide linker comprising the amino acid sequence AAALESR (SEQ ID NO:16); and
$X_6$ is a modified $O^6$-alkylguanine-DNA alkyltransferase;
(ii) transfecting a host cell with the expression vector of step (i);
(iii) expressing the recombinant polypeptide precursor by the host cell in a cell culture medium;
(iv) secreting the recombinant polypeptide precursor from the host cell into the supernatant of the cell culture medium using the secretion leader sequence;
(v) recovering the recombinant polypeptide precursor from the supernatant using the purification tag;
(vi) cleaving the recombinant polypeptide precursor with a protease to produce the mature recombinant polypeptide, wherein the mature polypeptide comprises $X_4$-$X_5$-$X_6$ of the recombinant polypeptide precursor; and
(vii) autoconjugating an $O^6$-benzylguanine-modified label to $X_6$.

12. The method of claim 11, wherein the secretion leader sequence is an Igk leader sequence.

13. The method of claim 11, wherein the purification tag is a 6x histidine tag.

14. The method of claim 11, wherein the protease cleavage site is an enterokinase cleavage site.

15. The method of claim 11, wherein the modified $O^6$-alkylguanine-DNA alkyltransferase is $O^6$-methylguanine-DNA methyltransferase.

16. The method of claim 11, wherein the $O^6$-benzylguanine-modified label is selected from the group consisting of Alexa Fluor 488, Alexa Fluor 633, Allophycocyanin (APC), APC-Cy7, Carboxyfluorescein Diacetate (CFSE), Cy3, Cy5, Fluorescein isothiocyanate (FITC), Peridinin chlorophyll protein (PerCP), Phycoerythrin (PE or R-PE), Phycoerythrin-Cy5, Phycoerythrin-Texas Red (PE-Texas Red) and Texas Red.

17. The method of claim 11, wherein the recombinant polypeptide precursor comprises the sequence of SEQ ID NO: 14.

18. The method of claim 11, wherein the host cell is a HEK293T cell.

19. The method of claim 11, wherein the recombinant polypeptide precursor is recovered from the supernatant by affinity chromatography.

20. A mature recombinant polypeptide capable of binding to phosphatidylserine, produced according to the method of claim 11.

21. A kit comprising the mature recombinant polypeptide of claim 20 and instructions for use.

22. An assay for detecting apoptosis in a cell population from a subject, comprising:
(i) contacting the cell population with the mature recombinant polypeptide of claim 20; and
(ii) detecting the binding of the phosphatidylserine binding ligand to phosphatidylserine on the cell surface,
wherein binding of the ligand is indicative of apoptosis in the cell population.

* * * * *